United States Patent [19]
Rizzoli et al.

[11] Patent Number: 5,287,524
[45] Date of Patent: Feb. 15, 1994

[54] EXTERNAL CIGARETTE CHECKING METHOD AND DEVICE

[75] Inventors: Salvatore Rizzoli, Bologna; Bruno Belvederi, S. Martino Di Monte S. Pietro, both of Italy

[73] Assignee: G. D Societa' Per Azioni, Bologna, Italy

[21] Appl. No.: 893,046

[22] Filed: Jun. 3, 1992

[30] Foreign Application Priority Data

Jun. 6, 1991 [IT] Italy .......................... B091A 000198

[51] Int. Cl.$^5$ .............................................. H04N 7/18
[52] U.S. Cl. ...................................... 348/86; 348/129
[58] Field of Search ................. 358/93, 101, 105, 106, 358/108

[56] References Cited

U.S. PATENT DOCUMENTS 4,492,476  1/1985  Miyazawa ......................... 358/106
4,776,466 10/1988  Yoshida ............................ 358/106
4,969,746 11/1990  McConnell et al. ............... 358/106
4,976,544 12/1990  Neri ................................. 358/106

FOREIGN PATENT DOCUMENTS 2201328  9/1988  United Kingdom .
2219395 12/1989  United Kingdom .
2221139  1/1990  United Kingdom .

*Primary Examiner*—Howard W. Britton
*Assistant Examiner*—Richard Lee
*Attorney, Agent, or Firm*—Sandler Greenblum & Bernstein

[57] ABSTRACT

A method and device for externally checking cigarettes, whereby the cigarettes, housed inside respective seats on a conveyor, are fed by the conveyor in a transverse direction in relation to the seats and along a path, one portion of which is a scanning path past a CCD scanning array; each cigarette being rotated at least 360° about its axis as it travels along the scanning path.

18 Claims, 3 Drawing Sheets

EXTERNAL CIGARETTE CHECKING METHOD AND DEVICE

BACKGROUND OF THE INVENTION

The present invention relates to a method of externally checking cigarettes.

Cigarettes are normally checked externally by feeding them successively and transversely along a given check path past an optical device, normally consisting of a telecamera, the images produced by which are compared with a reference image with which the cigarettes are to conform within acceptable limits. If they do not, the optical device emits signals which normally provide for subsequently rejecting the faulty cigarettes.

On known cigarette manufacturing machines, the cigarettes are normally fed along the check path by means of rollers with peripheral seats, each housing a respective cigarette, which is normally retained inside the seat by means of suction.

A major drawback of the above method of feeding the cigarettes along the check path is that the portion of the cigarette contacting the seat on the roller is hidden from view, so that any surface defects on the portion go undetected.

SUMMARY OF THE INVENTION

It is an object of the present invention to provide a method of externally checking cigarettes, designed to overcome the aforementioned drawback.

According to the present invention, there is provided a method of externally checking cigarettes, the method comprising steps including in feeding the cigarettes, housed inside respective seats on a conveyor, in a given direction and along a given path, one portion of which is a check path along which the external characteristics of each cigarette are checked; wherein the external characteristics are checked via optical detecting means located along the check path; each cigarette being rotated at least 360° about its axis as it travels along the check path.

The present invention also relates to a device implementing the above method.

According to the present invention, there is provided a device for externally checking cigarettes, the device comprising a conveyor having a number of seats, each housing a respective cigarette, and designed to move the seats in a given direction and along a given path, one portion of which is a check path along which the external characteristics of each cigarette are checked; wherein optical detecting means are located along the check path; and supporting and rotation means for each seat, for rotating each cigarette at least 360° about its axis as it travels along the check path.

BRIEF DESCRIPTION OF THE DRAWINGS

A non-limiting embodiment of the present invention will be described with reference to the accompanying drawings, in which.

DETAILED DESCRIPTION OF THE INVENTION

Figure 1:
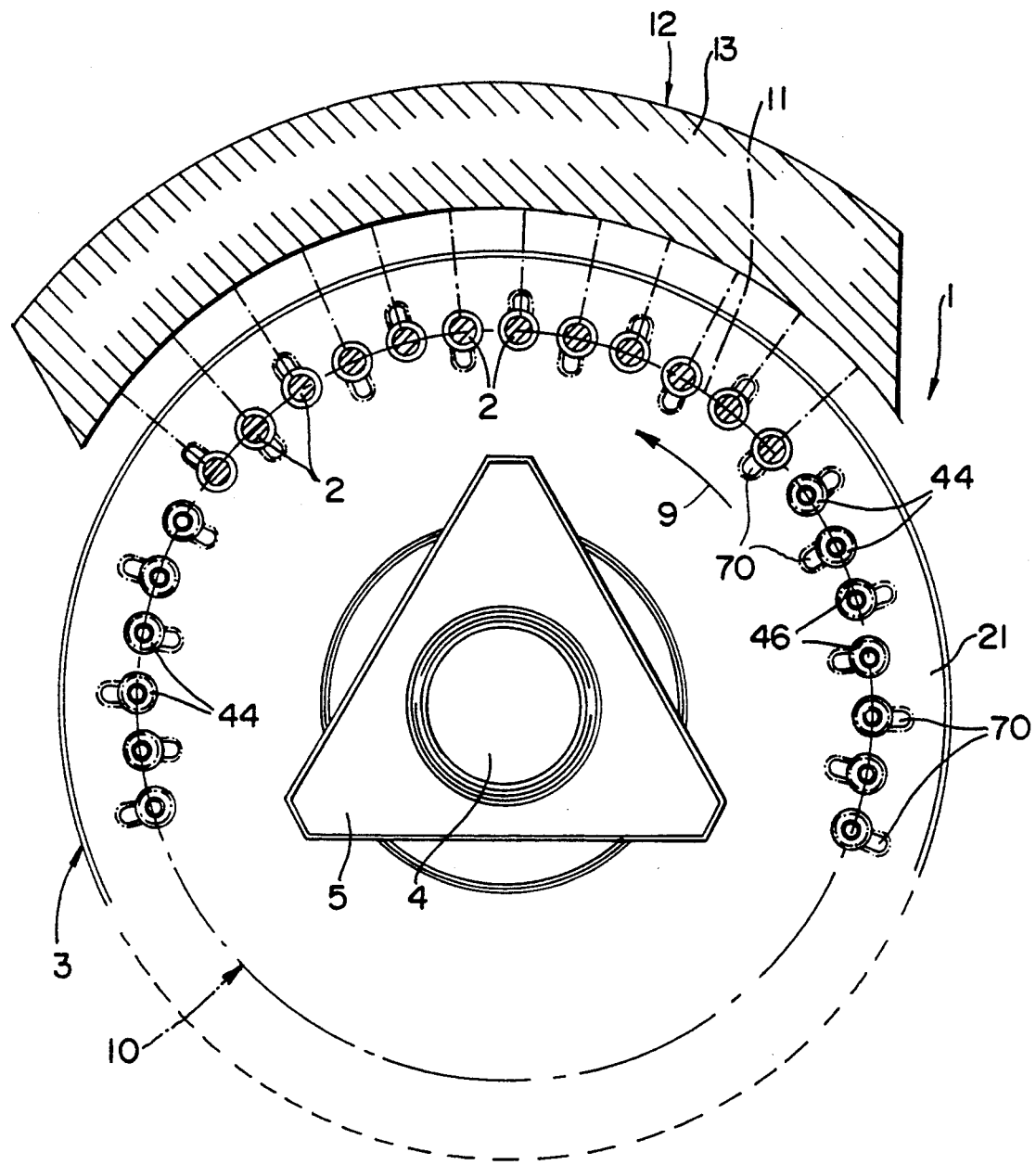
FIG. 1 shows a schematic side view, with parts removed for clarity, of a preferred embodiment of the device according to the present invention.

Number 1 in FIG. 1 indicates a device for externally checking cigarettes 2 (FIG. 2) fed successively to device 1 on known conveyors (not shown), as well as, in the specific example shown, for checking the air permeability of cigarettes 2.

Figure 2:
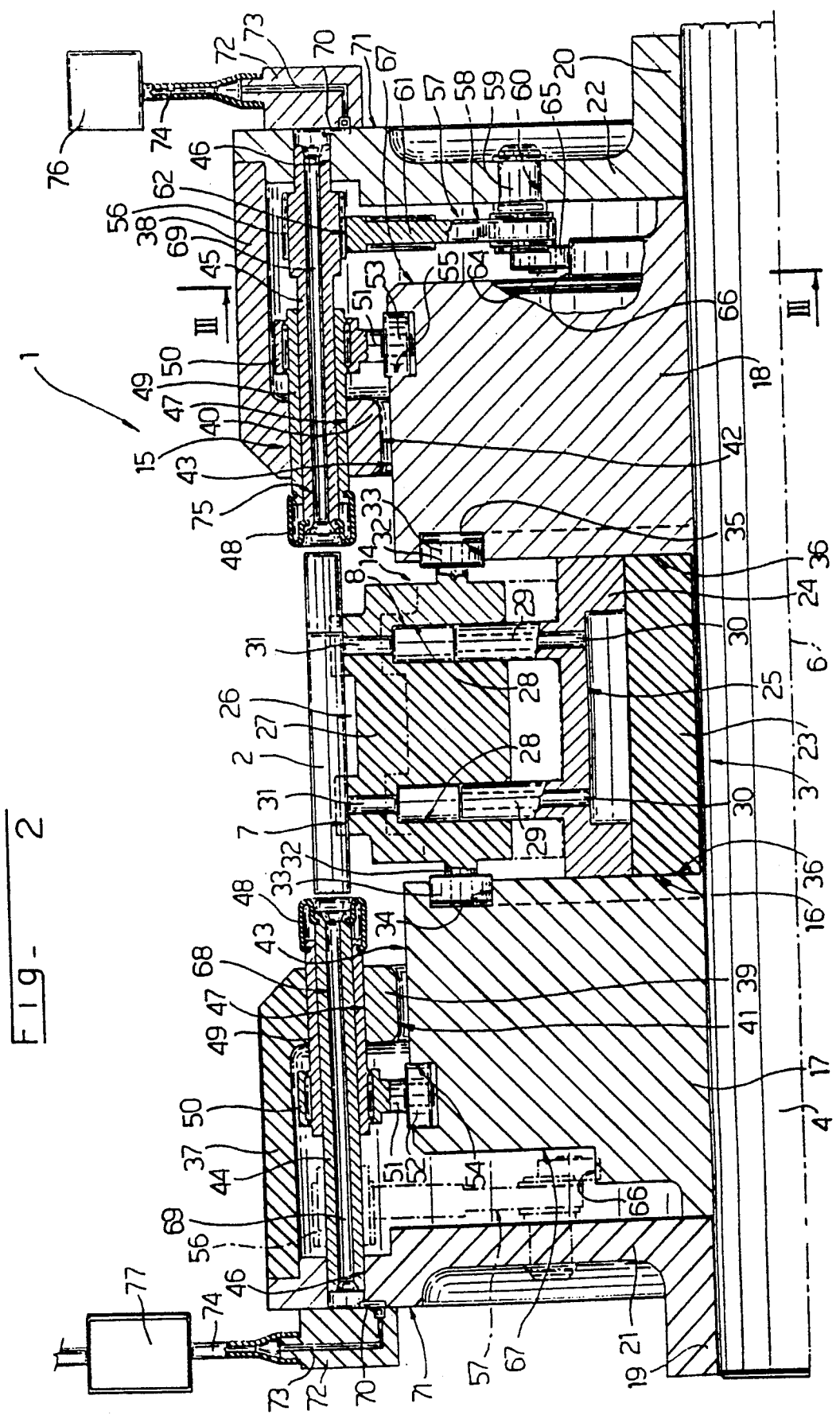
FIG. 2 shows an enlarged half cross section of the FIG. 1 device.

As shown in FIG. 2, device 1 comprises a conveyor including a roller 3 fitted on to a powered shaft 4 supported for rotation on a fixed frame (not shown) via a flanged tubular element 5 (FIG. 1), and designed to rotate roller 3 about its axis 6.

Roller 3 presents a number of peripheral seats 7 (only one of which is shown in FIG. 2), each housing a respective cigarette 2, which is maintained contacting the edge of roller 3 by means of a suction device indicated as a whole by 8.

As shown in FIG. 1, roller 3 is designed to move seats 7 in an anticlockwise direction 9 along a circular path 10, a central portion of which consists of a check or scanning path 11 (shown by the double dotted line in FIG. 1) along which both the external characteristics and air permeability of each cigarette 2 are checked.

For this purpose, device 1 comprises optical detecting means including a scanning camera 12 comprising a known CCD array 13 and located along scanning path 11 for performing a given number of sweeps over each cigarette 2. Such scanning provides for detecting any surface defects (not illustrated) on cigarettes 2, such as clogged or poorly formed ventilation holes, poor gumming, printing defects (position and/or intensity), etc., and for emitting, in known manner, signals which may be employed, for example, for activating a reject device (not shown) downstream from device 1.

To enable telecamera 12 to examine the whole surface of each cigarette 2, roller 3 comprises, for each seat 7, a spacing unit 14 for detaching cigarette 2 from seat 7 as it is fed by roller 3 along scanning path 11. More specifically, unit 14 provides for moving seat 7 radially in relation to shaft 4, between an engaged position wherein seat 7 is located along path 10 and contacting cigarette 2, and a detached position wherein cigarette 2 is located on, and seat 7 a given distance from, path 10.

For supporting cigarette 2 in the detached position, as it is fed along scanning path 11, roller 3 comprises a supporting and rotation device 15 for engaging the opposite ends of cigarette 2 as it engages path 11, and rotating it at least 360° about its axis as it travels along path 11.

As each seat 7 engages scanning path 11, herefore, device 15 is activated so as to engage the opposite ends of cigarette 2 and hold it in position on path 10 when seat 7 is detached by unit 14. Once cigarette 2 is detached from seat 7 and so free to rotate about its axis without rubbing against seat 7, device 15 is activated so as to rotate cigarette 2 at least 360° about its axis in the time taken for it to travel along path 11, and before seat 7 is restored to the engaged position.

By virtue of being rotated as described above, substantially the whole surface of each cigarette 2 fed by roller 3 along path 10 is scanned by telecamera 12, with no harmful stress being transmitted to the cigarette and, what is more, with no danger of any surface portions of the cigarette escaping inspection.

Figure 3:
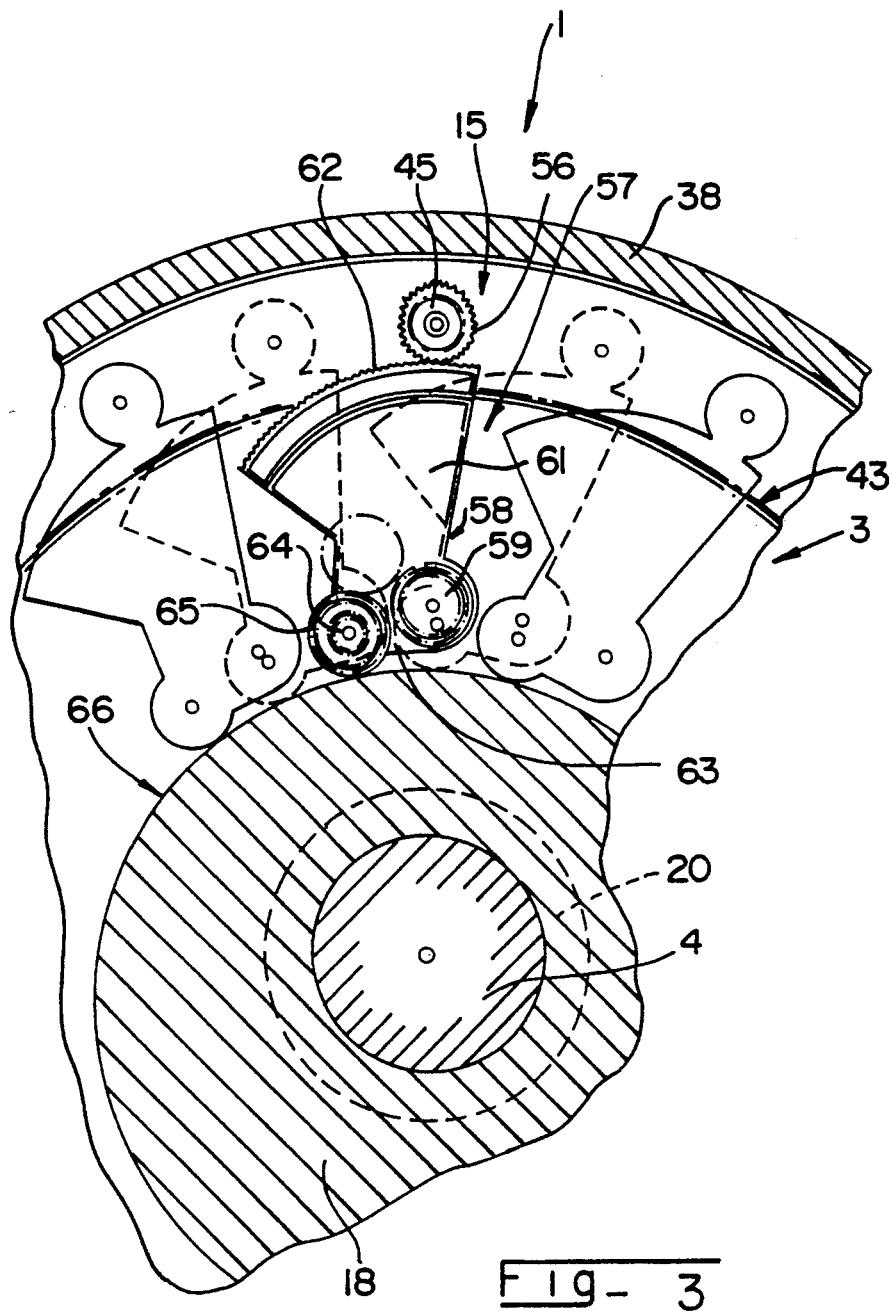
FIG. 3 shows a section along line III—III in FIG. 2.

In the specific embodiment shown in FIGS. 2 and 3, roller 3 comprises an intermediate annular body 16 coaxial with shaft 4; two drum-shaped cams 17 and 18 coaxial with axis 6 and fitted on to shaft 4 on either side of intermediate annular body 16; and two sleeves 19 and 20 fitted on to shaft 4 outwards of cams 17 and 18 respectively, and having respective annular flanges 21 and 22.

Intermediate annular body 16 comprises a known fixed air distributor 23 coaxial with shaft 4; an inner ring 24 connected angularly in known manner (not show) to shaft 4, and extending outwards of distributor 23 so as to define, with the same, a number of chambers 25 (only one of which is shown in FIG. 2) selectively communicating, via distributor 23 and along given portions of path 10, with a known suction member (not shown); and an outer ring 26 defined by a number of sectors 27 (only one of which is shown in FIG. 2), each having an outer transverse groove defining a respective seat 7, and two radial holes 28, each engaged in sliding and fluidtight manner by a respective appendix 29 extending radially outwards from inner ring 24 and acting as a drive key for angularly connecting sector 27 to inner ring 24.

Each appendix 29 presents an axial through hole 30 communicating at one end with a respective chamber 25 and at the other with a hole 31 formed radially through respective sector 27 and terminating at the bottom of respective seat 7.

Distributor 23, the suction member (not shown) of distributor 23, chambers 25 and holes 30 and 31 together constitute suction device 8 on roller 3 for retaining cigarettes 2 inside respective seats 7 over specific portions of path 10.

As shown in FIG. 2, each sector 27 presents two coaxial lateral appendixes 32 parallel to axis 6, supporting for rotation respective tappet rollers 33 on either side of intermediate annular body 16, and engaged inside respective cam grooves 34 and 35 formed on the inner lateral surfaces 36 of respective cams 17 and 18.

Sectors 27, respective appendixes 32 and tappet rollers 33, and cam grooves 34 and 35 combine to define spacer unit 14; and identical cam grooves 34 and 35 are so formed as to maintain each sector 27 in a normal raised position (shown by the continuous line in FIG. 2), wherein seat 7 engages cigarette 2, as sector 27 travels over the nonscanning portion of path 10, and to move each sector 27 into a lowered operating position (shown by the dot-and-dash line in FIG. 2), wherein seat 7 is detached from cigarette 2, as sector 27 travels along scanning path 11.

Sleeves 19 and 20 and respective flanges 21 and 22 form part of supporting and rotation device 15, which, as shown in FIG. 2, also comprises two opposed bells 37, 38 having the open end connected to the outer edge of respective flanges 21, 22, and closed at the other end by respective end walls 39, 40 having respective central through holes 41, 42 engaged in rotary manner and with a given radial clearance by the outer cylindrical surface 43 of respective cams 17, 18.

For each sector 27, device 15 also comprises two coaxial rods 44, 45 parallel to axis 6 and coaxial with respective seat 7 in the engaged position. Rods 44, 45 define respective slides, each extending in axially-sliding manner through a respective guide defined by a hole 46 formed through respective flange 21, 22, and by a hole 47 formed in respective end wall 39, 40. The end of each rod 44, 45 facing respective sector 27 is fitted rigidly with a tubular housing 48 of resilient material for receiving and angularly clamping a respective end of cigarette 2. Rods 44, 45 support, in rotary and axially-fixed manner, respective tubular outer bodies 49, each connected for rotation, via the interposition of a rotary ring (not shown), to respective housing 48, and each fitted with an outer ring 50 having an outer radial appendix 51 between respective holes 46 and 47. Appendixes 51 support for rotation respective tappet rollers 52, 53 engaging respective cam grooves 54, 55 formed on the outer surface 43 of respective cams 17, 18.

Grooves 54 and 55 are so formed as to maintain housings 48 in a detached idle position (FIG. 2) wherein they are detached from the ends of cigarette 2, as respective sector 27 travels over the nonscanning portion of path 10; and to move housings 48 into an engaged operating position (not shown) wherein they engage the respective ends of cigarette 2, just before spacer unit 14 is activated for lowering sector 27, and to detach housings 48 as soon as sector 27 is restored by unit 14 to the raised position.

Device 15 thus provides for supporting cigarettes 2 when detached from respective seats 7 over scanning portion 11 of path 10.

Each of coaxial rods 44, 45 is fitted with a gear 56, which, as shown more clearly in FIG. 3, meshes with a respective actuating device 57 by which rods 44, 45, angularly connected by cigarette 2 in the engaged position, are rotated at least 360° about their axis as respective sector 27 travels over scanning portion 11.

Each actuating device 57 comprises a rocker arm 58 pivoting centrally on respective flange 21, 22 via a pin 59 engaged in rotary manner inside a hole 60 (FIG. 2) formed through flange 21, 22 and parallel to axis 6. Rocker arm 58 comprises a first arm 61, the free end of which is defined by a sector gear 62 meshing with respective gear 56; and a second arm 63 supporting a fixed pin 64 in turn supporting in rotary manner a tappet roller 65 engaging a cam groove 66 formed on the outer lateral surface 67 of respective cam 17, 18.

Each groove 66 is so formed as to rotate each gear 56 at least 360° as respective sector 27 travels over scanning portion 11, and so enable telecamera 12 to scan the entire surface of cigarette 2.

In the embodiment shown, by virtue of employing housings 48 of resilient material, designed to mate both angularly and in fluidtight manner with cigarettes 2, supporting and rotation device 15 may be combined with a control device 68 for determining the air permeability of cigarettes 2.

According to a variation not shown, control device 68 (which is known) is detached from device 15 and mounted on a further roller (not shown) up- or downstream from roller 3.

As shown in FIG. 2, for each pair of coaxial rods 44, 45, control device 68 comprises a hole 69 formed axially along each rod 44, 45 and communicating at one end with respective housing 48, and at the other with the end of respective hole 46; a groove 70 formed on the outer surface 71 of each flange 21, 22 and extending radially from the edge of respective hole 46; and a fixed block 72 connected in sliding and fluidtight manner to surface 71 of each flange 21, 22.

Each block 72 presents a through hole 73 communicating successively at one end with groove 70 in respective flange 21, 22, and at the other with a conduit 74.

Holes 69, when communicating pneumatically with each other via cigarette 2 engaged by rods 44, 45 over scanning portion 11, and with respective holes 73 and conduits 74, define a pneumatic circuit 75 connected at one end to a known pump means 76 and at the other to an exhaust via a known gauge 77 for detecting the pressure in circuit 75 and emitting, in known manner, an analog signal which, if outside a given range of values, may be employed for subsequently rejecting cigarette 2.

We claim:

1. A method for externally checking cigarettes, said method comprising the steps of:

feeding the cigarettes housed inside respective seats on a conveyor, in a travelling direction and along a predetermined path, one portion of said predetermined path being a check path along which external characteristics of each of said cigarettes is checked;

checking the external characteristics via optical detecting means located along said check path;

detaching each of said cigarettes from a respective seat as it travels along said check path; and rotating each of said cigarettes at least 360° about its axis as it travels along said check path, wherein each of said cigarettes are rotated about its axis while being detached from its respective seat.

2. A method as claimed in claim 1, wherein said check path is a scanning path; said optical detecting means for detecting said external characteristics comprising tele-camera means.

3. A method as claimed in claim 2, wherein said tele-camera means comprises a CCD scanning array along said check path.

4. A method as claimed in claim 1, comprising detaching each of said cigarettes from a respective seat by connecting each of said cigarettes along said check path to a supporting and rotation device, said supporting and rotation device being supported on and moving with said conveyor for supporting each of said cigarettes along said check path, and detaching a respective seat from each of said cigarettes.

5. A method as claimed in claim 4, comprising detaching each of said respective seats from each of said cigarettes along said check path by moving said seat perpendicularly in relation to said check path.

6. A method as claimed in claim 4, comprising providing in a detached position each of said cigarettes with a pneumatic circuit for determining air permeability of each of said cigarettes.

7. A method as claimed in claim 6, comprising extending part of said pneumatic circuit through said supporting and rotation device, said supporting and rotation device comprising engaging means moving to and from a position for engagement of each of said cigarettes both angularly and in a fluidtight manner; said engaging means being moved into an engaged position as each of said cigarettes travels along said check path; and said pneumatic circuit extending through each of said cigarettes when said engaging means are moved into said engaged position.

8. A device for externally checking cigarettes, said device comprising:

a conveyor having a predetermined number of seats, each seat housing a respective one of said cigarettes and designed to move said seats in a travelling direction and along a predetermined path, one portion of said predetermined path being a check path along which external characteristics of each of said cigarettes are checked;

optical detecting means being located along said check path;

supporting and rotation means for each of said seats for rotating each of said cigarettes at least 360° about its axis as said cigarettes travel along said check path; and spacer means for each of said seats for detaching each of said cigarettes from each of said seats as each of said cigarettes is rotated about its axis and travels along said check path.

9. A device as claimed in claim 8, said check path being a scanning path; said optical detecting means for detecting said external characteristics comprising tele-camera means.

10. A device as claimed in claim 9, wherein said tele-camera means comprises a CCD scanning array along said check path.

11. A device as claimed in claim 8, wherein said conveyor comprises a roller having an axis, said roller rotating about said axis in said traveling direction; and said predetermined path being circular.

12. A device as claimed in claim 11, wherein said roller comprises an outer ring defined by a predetermined number of adjacent sectors, each having a respective one of said seats; said spacer means being connected to each one of said sectors for moving one of said sectors between a normal operating position, wherein each of said seats is located along said predetermined path, and a detached position wherein each of said seats is moved towards said axis in relation to said predetermined path.

13. A device as claimed in claim 12, wherein said spacer means comprises cam means connected to each one of said sectors, for moving each one of said sectors into said detached position as it travels along said check path.

14. A device as claimed in claim 8, wherein, for each one of said seats, said supporting and rotation means comprises two coaxial guide means located on either side of the seat and integral with and moving with said conveyor along said predetermined path; two slide means being coaxial with said seat when said seat is located on said predetermined path, and each slide means being connected in a rotary and axially-sliding manner to a respective said coaxial guide means; engaging means on each said slide means for angularly engaging a respective end of each of said cigarettes housed inside said seat and located on said predetermined path; first actuating means for moving said slide means to and from a position wherein each of said cigarettes is engaged by said engaging means; and second actuating means connected to said slide means, for rotating said slide means at least 360° about their common axis and in relation to said guide means.

15. A device as claimed in claim 14, wherein said engaging means are made of resilient material and engage a respective end of each of said cigarettes angularly and in a fluidtight manner.

16. A device as claimed in claim 15, further comprising a control device for determining the air permeability of each of said cigarettes; said control device comprising a pressurized fluid source; a pressure gauge; and, pneumatic circuit means extending through said slide means and said engaging means, for connecting said pressurized fluid source to said pressure gauge via each of said cigarettes when said engaging means are in an engaged position.

17. A method for externally checking cigarettes, the method comprising the steps of:

advancing the cigarettes in a predetermined direction and along a travelling path by means of a conveyor having transverse seats, each one of said seats accommodating a respective one of said cigarettes, each one of said seats extending parallel to a longitudinal axis of a respective one of said cigarettes, and being arranged in contact with a lateral surface thereof, and one portion of said travelling path being a check path along which external characteristics of each of said cigarettes are checked;

detaching each of said cigarettes from a respective seat as it travels along said check path;

checking the external characteristics of each of said cigarettes by means of optical detecting means located along said check path; and rotating each of said cigarettes at least 360° about its longitudinal axis while being detached from said respective seat and being checked.

18. A method for externally checking cigarettes, the method comprising the steps of:

advancing the cigarettes in a predetermined direction and along a travelling path by means of a conveyor having transverses seats, each one of said seats accommodating a respective one of said cigarettes, each one of said seats extending parallel to a longitudinal axis of a respective one of said cigarettes, and being arranged in contact with a lateral surface thereof, and one portion of said travelling path being a check path along which external characteristics of each of said cigarettes are checked;

detaching each of said cigarettes from a respective seat as it travels along said check path;

checking the external characteristics of each of said cigarettes by means of optical detecting means located along said check path; and rotating each of said cigarettes at least 360° about its axis in relation to a respective one of said seats while being detached from a respective seat and being checked.

* * * * *